US007556837B2

(12) United States Patent
Hossainy

(10) Patent No.: US 7,556,837 B2
(45) Date of Patent: Jul. 7, 2009

(54) METHOD FOR COATING STENTS

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/014,029

(22) Filed: Jan. 14, 2008

(65) Prior Publication Data

US 2008/0107795 A1 May 8, 2008

Related U.S. Application Data

(62) Division of application No. 10/266,479, filed on Oct. 8, 2002, now Pat. No. 7,335,265.

(51) Int. Cl.
*A61L 33/00* (2006.01)

(52) U.S. Cl. ......................... 427/2.24; 427/8; 427/2.21; 427/2.1; 427/2.25; 427/421.1; 118/668; 118/500; 118/504; 118/505; 623/1.46; 623/1.47; 623/1.48; 606/194

(58) Field of Classification Search ................. 118/500, 118/668; 427/2.24
See application file for complete search history.

(56) References Cited

U.S. PATENT DOCUMENTS

| | | | |
|---|---|---|---|
| 3,827,139 | A | 8/1974 | Norteman |
| 4,082,212 | A | 4/1978 | Headrick et al. |
| 4,290,383 | A | 9/1981 | Pfender |
| 4,629,563 | A | 12/1986 | Wrasidlo |
| 4,733,665 | A | 3/1988 | Palmaz |
| 4,800,882 | A | 1/1989 | Gianturco |
| 4,886,062 | A | 12/1989 | Wiktor |
| 4,906,423 | A | 3/1990 | Frisch |
| 4,955,899 | A | 9/1990 | Della Corna et al. |
| 5,033,405 | A | 7/1991 | Yamada et al. |
| 5,037,427 | A | 8/1991 | Harada et al. |
| 5,171,445 | A | 12/1992 | Zepf |
| 5,188,734 | A | 2/1993 | Zepf |
| 5,201,314 | A | 4/1993 | Bosley et al. |
| 5,229,045 | A | 7/1993 | Soldani |
| 5,234,457 | A | 8/1993 | Andersen |
| 5,421,955 | A | 6/1995 | Lau et al. |
| 5,458,683 | A | 10/1995 | Taylor et al. |
| 5,478,349 | A | 12/1995 | Nicholas |
| 5,537,729 | A | 7/1996 | Kolobow |
| 5,607,442 | A | 3/1997 | Fischell et al. |
| 5,611,775 | A | 3/1997 | Machold et al. |
| 5,624,411 | A | 4/1997 | Tuch |

(Continued)

OTHER PUBLICATIONS

U.S. Appl. No. 10/255,913, Tang et al., filed Sep. 26, 2002.

*Primary Examiner*—Michael Barr
*Assistant Examiner*—Andrew Bowman
(74) *Attorney, Agent, or Firm*—Squire, Sanders & Dempsey, L.L.P.

(57) ABSTRACT

An apparatus for coating implantable medical devices, such as stents, and a method of coating stents using the apparatus is also disclosed. The apparatus includes a barrier or barriers for isolating an area of the stent on which a composition for coating a stent is applied. Two coating compositions can be applied simultaneously to a stent by separate nozzles on different sides of a barrier. Cross-contamination of the compositions is prevented by the barrier.

10 Claims, 2 Drawing Sheets

U.S. PATENT DOCUMENTS

| | | | |
|---|---|---|---|
| 5,628,786 A | 5/1997 | Banas et al. | |
| 5,687,906 A | 11/1997 | Nakagawa | |
| 5,713,949 A | 2/1998 | Jayaraman | |
| 5,772,864 A | 6/1998 | Møller et al. | |
| 5,788,626 A | 8/1998 | Thompson | |
| 5,820,917 A | 10/1998 | Tuch | |
| 5,823,996 A | 10/1998 | Sparks | |
| 5,833,659 A | 11/1998 | Kranys | |
| 5,855,598 A | 1/1999 | Pinchuk | |
| 5,865,814 A | 2/1999 | Tuch | |
| 5,891,108 A | 4/1999 | Leone et al. | |
| 5,895,407 A | 4/1999 | Jayaraman | |
| 5,897,911 A | 4/1999 | Loeffler | |
| 5,902,631 A | 5/1999 | Wang et al. | |
| 5,922,393 A | 7/1999 | Jayaraman | |
| 5,935,135 A | 8/1999 | Bramfitt et al. | |
| 5,948,018 A | 9/1999 | Dereume et al. | |
| 6,010,573 A | 1/2000 | Bowlin | |
| 6,045,899 A | 4/2000 | Wang et al. | |
| 6,056,993 A | 5/2000 | Leidner et al. | |
| 6,068,202 A | 5/2000 | Hynes et al. | |
| 6,106,889 A | 8/2000 | Beavers et al. | |
| 6,120,847 A | 9/2000 | Yang et al. | |
| 6,126,686 A | 10/2000 | Badylak et al. | |
| 6,153,252 A | 11/2000 | Hossainy et al. | |
| 6,156,373 A | 12/2000 | Zhong et al. | |
| 6,214,115 B1 | 4/2001 | Taylor et al. | |
| 6,228,072 B1 | 5/2001 | Omaleki et al. | |
| 6,245,099 B1 | 6/2001 | Edwin et al. | |
| 6,258,121 B1 | 7/2001 | Yang et al. | |
| 6,273,878 B1 | 8/2001 | Muni | |
| 6,279,368 B1 | 8/2001 | Escano et al. | |
| 6,322,847 B1 | 11/2001 | Zhong et al. | |
| 6,364,903 B2 | 4/2002 | Tseng et al. | |
| 6,387,118 B1 | 5/2002 | Hanson | |
| 6,521,284 B1 | 2/2003 | Parsons et al. | |
| 6,527,863 B1 | 3/2003 | Pacetti et al. | |
| 6,565,659 B1 * | 5/2003 | Pacetti et al. | 118/500 |
| 6,572,644 B1 | 6/2003 | Moein | |
| 6,605,154 B1 | 8/2003 | Villareal | |
| 6,610,087 B1 | 8/2003 | Zarbatany et al. | |
| 6,673,154 B1 | 1/2004 | Pacetti et al. | |
| 6,676,700 B1 | 1/2004 | Jacobs et al. | |
| 6,695,920 B1 | 2/2004 | Pacetti et al. | |
| 6,818,063 B1 | 11/2004 | Kerrigan | |
| 2001/0037145 A1 | 11/2001 | Guruwaiya et al. | |
| 2003/0207019 A1 * | 11/2003 | Shekalim et al. | 427/2.24 |
| 2006/0079953 A1 | 4/2006 | Gregorich et al. | |

* cited by examiner

METHOD FOR COATING STENTS

This application is a divisional of U.S. patent application Ser. No. 10/266,479, filed Oct. 8, 2002, now U.S. Pat. No. 7,335,265 the entire disclosure of which is incorporated herein by reference.

BACKGROUND OF THE INVENTION

1. Field of the Invention

This invention relates to methods for coating implantable medical devices, such as stents.

2. Description of the Background

FIG. 1 illustrates a conventional stent 10, which includes connected struts 12 forming a tubular expandable body. Stent 10 functions as a scaffolding structure for physically holding open the wall of a blood vessel or other bodily lumen. Stent 10 is capable of being compressed, so that stent 10 can be inserted through small lumens via catheters, and then expanded to a larger diameter once it is at the desired location. Mechanical intervention via stents has reduced the rate of restenosis as compared to balloon angioplasty; restenosis, however, is still a significant problem. Moreover, treating restenosis in stented vessels can be challenging, as clinical options are more limited as compared to lesions that were treated solely with a balloon.

In order to more effectively treat restenosis, stent implantation procedures are being supplemented with a pharmaceutical regimen. Systemic administration of drugs for the treatment of restenosis can produce adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Being made of metal, stents need to be modified so as to provide a suitable means of locally delivering a drug. A polymeric coated stent has proved to be a very effective way of allowing a stent to locally deliver a drug. A solution of a polymer dissolved in a solvent and a therapeutic substance added thereto is applied to the stent. The composition is applied to the stent by spraying the composition on the stent or immersing the stent in the composition. Once the solvent evaporates, a polymeric coating impregnated with a therapeutic substance remains on the surface of the stent. The coating provides for a sustained release of the therapeutic substance at the treatment site.

To the extent that the mechanical functionality of stents has been optimized, continued improvements can be made to the coating of the stent. A coating design is needed that is capable of releasing more than one therapeutic substance to the treatment site. Accordingly, conditions other than restenosis, such as excessive inflammation or thrombosis, can also be addressed. Moreover, the coating should be capable of releasing a single drug or more than one drug at different release rates. For example, a coating should be capable of releasing a steroidal anti-inflammatory substance immediately subsequent to the stent implantation and releasing a drug for inhibiting migration and proliferation of vascular smooth muscle cells at a slower release rate for a prolonged duration of time. Accordingly, a more customized treatment regimen for the patient can be provided. The present invention provides an apparatus that can produce a coating that addresses these needs and provides other improved coating designs for drug eluting vascular stents.

SUMMARY

The present invention is generally directed to a method for coating a stent. In aspects of the present invention, the method comprises applying a first composition to a first segment of a stent with a first nozzle assembly, and simultaneously with the application of the first composition, applying a second composition to a second segment of the stent with a second nozzle assembly. In detailed aspects, the second segment of the stent does not get exposed or significantly exposed to the first composition and wherein the first segment of the stent does not get exposed or significantly exposed to the second composition when both compositions are being applied simultaneously. In further detailed aspects, the first composition is different from the second composition in type of polymer, type of therapeutic substance, or concentration of therapeutic substance.

In other aspects of the present invention, the method comprises positioning the stent through a through hole formed in a barrier such that a first surface of the barrier faces one end of the stent and a second surface of the barrier faces an opposing end of the stent, positioning a nozzle relative to the barrier such that the barrier shields a first area of the stent to which a coating substance is not be applied and the barrier does not shield a second area of the stent to which the first coating substance is to be applied, and delivering the coating substance from the nozzle to the second area of the stent. In further aspects, the method comprises positioning a second nozzle relative to the barrier to allow application of a second coating substance from the second nozzle to the first area of the stent but not the second area of the stent. In still further aspects, the method comprises delivering the second coating substance from the second nozzle to the first area of the stent, and preventing or significantly minimizing cross-contamination of the coating substance from the nozzle and the second coating substance from the second nozzle as the coating substances are applied to the stent.

The features and advantages of the invention will be more readily understood from the following detailed description which should be read in conjunction with the accompanying drawings.

DETAILED DESCRIPTION

Figure 1:
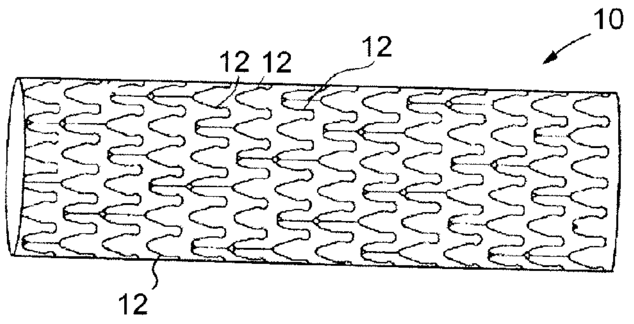
FIG. 1 Prior Art
FIG. 1 illustrates a conventional stent.
Figure 2:
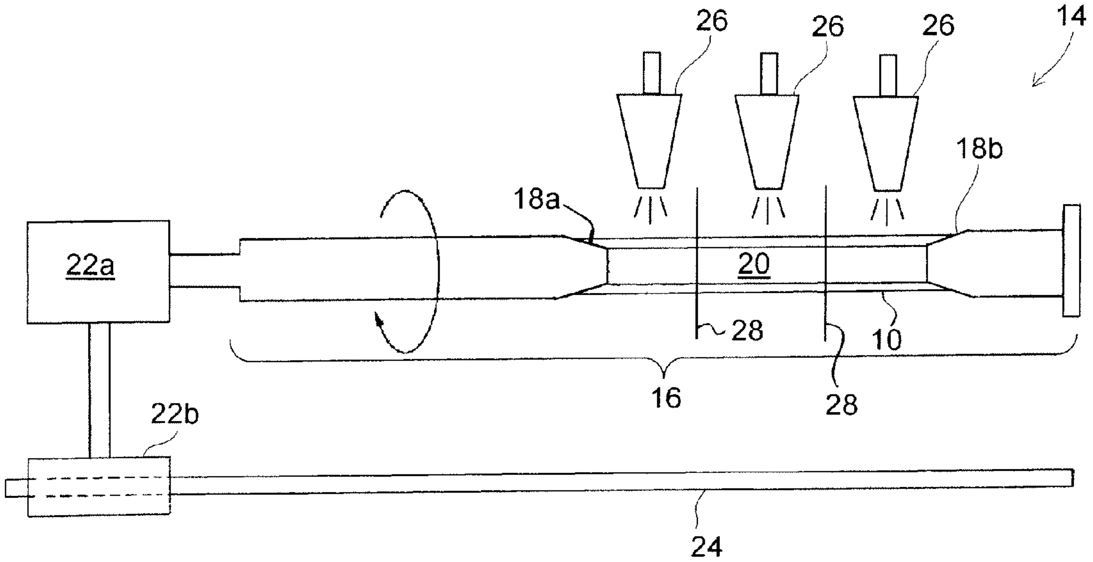
FIG. 2 illustrates one embodiment of the coating apparatus of the present invention.

FIG. 2 illustrates one embodiment of a coating system 14 for depositing a coating on stent 10. Although the present invention is described with reference to a stent, system 14 can also be used to coat a variety of other implantable medical devices, such as stent-grafts and grafts. Stent 10 can have any stent design and the structure is not limited to the illustration of FIG. 1. Stent 10 can be made from any suitable material, such as stainless steel. A mandrel 16 supports stent 10 during the coating process. Mandrel 16 includes two opposing conically shaped ends 18*a* and 18*b* that can penetrate at least partially within ends of stent 10. A bar portion 20 extending through the longitudinal bore of stent 10 connects ends 18*a* and 18*b* to one another. The connection of bar 20 with ends 18*a* or 18*b* can be via a friction fit or a screw fit so that ends 18*a* and 18*b* are not only capable of disengaging from bar portion 20 but also are capable of being moved incrementally closer together for securely pinching stent 10. Mandrel 16 can be coupled to a first motor assembly 22*a* for providing rotation motion to stent 10. A second motor 22*b* can be optionally provided for moving stent 10 in a linear direction along rail 24.

A set of nozzles 26 is provided for applying a coating composition to stent 10. Although FIG. 2 illustrates three nozzles, any suitable number of nozzles 26 can be used. Nozzles 26 can be, for example, model #780S external air mixing nozzles from EFD Inc., East Providence, R.I., or 8700-25, 8700-35, 8700-48, 8700-48H, or 8700-60 ultrasonic nozzles from Sono-Tek Corp., Milton, N.Y, that can be used in conjunction with an air focus shroud (not shown) to help direct the spray to the target, for example, the AccuMist system also from Sono-Tek Corp. Each nozzle 26 can have its own spray characteristics.

Nozzles 26 can eject a spray of a solution that spreads angularly as the spray moves away from nozzle 26. As the cross-sectional area of the spray grows with respect to the distance away from nozzle 26, the flux of the spray can be larger near the center of the cross-section of the spray and smaller near the edges of the cross-section of the spray, where the cross-section is taken perpendicular to the direction of the spray. The variability of the spray flux can produce a coating layer on stent 10 that is thicker directly under nozzle 26 and thinner further away from nozzle 26. The uneven thickness of the layer can be minimized by making the spray angle wider. Nozzles 24 can be placed any suitable distance away stent 10 so that the application of the coating material is contained within the boundaries provided by barriers 28. The selected distance, therefore, can be a function of a variety of factors, including spray characteristics of nozzle 26, the viscosity of the composition, spray flux, and the like. The distance can be, for example, from about 3 cm to about 15 cm.

Figure 3:
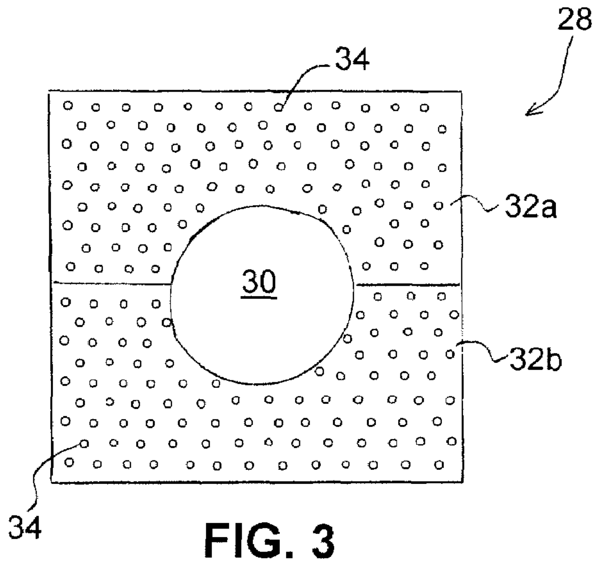
FIG. 3 illustrates a side view of one embodiment of the barrier used with the coating apparatus.

As further illustrated by FIG. 2, nozzles 26 are separated by barriers 28. As illustrated by FIG. 3, barrier includes an opening 30 through which stent 10 is positioned. The size of opening 30 should be large enough to provide a suitable clearance between the outer surface of stent 10 and barrier 28, but also small enough to prevent cross contamination of the coating substance from the adjacent spray nozzles 26. The size of opening 30 will of course depend on the diameter of stent 10 as mounted on mandrel 16. Barrier 28 can be made from 2 pieces, upper part 32*a* and lower part 32*b*, which can be securely joined together. Barriers 28 can be made of any suitable material, for example, stainless steel. In one embodiment, barriers 28 can have pores 34 on the surface for preventing at least some of the coating composition from gathering and dripping on stent 10. Alternatively, barriers 28 can be made from an absorbent material, such as a sponge, or the surface of barriers 28 can be coated with an absorbent material for preventing at least some of the composition from dripping onto stent 10. The distance between barriers 28 can be adjusted so that nozzles 26 can cover any desired length of stent 10. The distance could be adjusted during the application of the composition, or alternatively, the application of the composition can be terminated and then the distance adjusted.

In accordance with another embodiment, precision nozzles can be used, with or with out a barrier so as to only cover a selected length of stent with the coating composition. The coating sprayed by the precision nozzles can have a minimally varying diameter of the spray when the spray reaches stent 10. The predictability of the spray's coverage enables the application of multiple coated regions without barriers. The precision nozzle can also create a spray with a substantially even flux distribution throughout the cross-section of the spray. Precision nozzles can be, for example, 8700-35, 8700-48, 8700-48H, or 8700-60 ultrasonic nozzles from Sono-Tek Corp., Milton, N.Y.

Figure 4A:
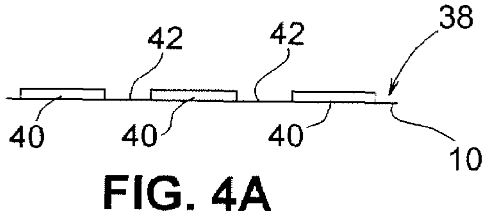
FIGS. 4A to 4F present various coating deposits that can be formed by the apparatus of the present invention.
Figure 4B:
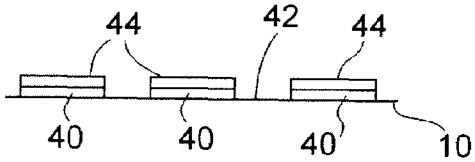
Figure 4C:
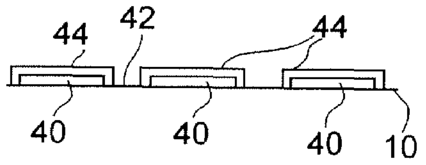
Figure 4D:
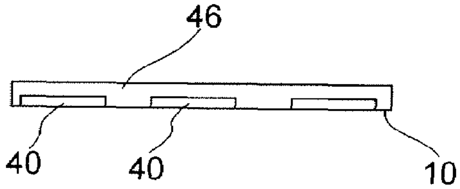

Coating system 14 can be used to deposit a variety of coating patterns onto stent 10. FIGS. 4A to 4F illustrate several embodiments of coating patterns that can be produced. FIG. 4A illustrates stent surface 38 having an intermittent pattern of polymer layers 40 separated by bare stent regions 42. Bare stent regions 42 are areas which were masked by barriers 28 during the coating process. The length of bare regions 42 between layers 40 has been exaggerated for illustrative purposes. Each of layers 40 can include a different polymer and optionally a therapeutic substance, which can also be different for each layer 40. Each nozzle 26 can also deposit a different concentration of a therapeutic substance for each layer 40. Accordingly, stent 10 will have different concentration of a therapeutic substance in different areas of stent 10. FIGS. 4B and 4C illustrate layers 44 deposited over layers 40. Each of layers 44 can include a different polymer and optionally a therapeutic substance, which can also be different for each layer 44. By adjusting coating parameters, such as distance of nozzles 26 from stent 10, the viscosity of the coating composition, etc., layers 44 can be deposited to extend beyond sidewalls of layers 40. In accordance to yet another embodiment, as illustrated in FIG. 4D, a topcoat layer 46 can be uniformly deposited over layers 40. Topcoat layer 46 can serve as a rate-limiting barrier for the release of the drug. Accordingly, if layers 40 are each made from a different polymeric material and contain a different drug, stent 10 can release each of the different drugs at a different release rate for a prolonged duration of time.

Figure 4E:
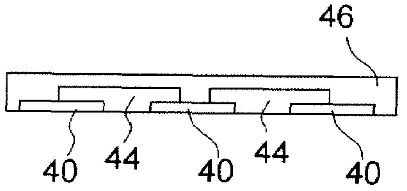
Figure 4F:
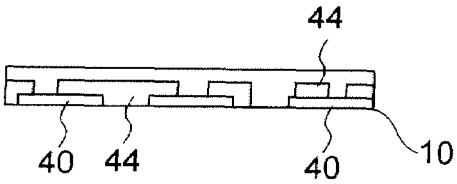

As mentioned before, the positioning of barriers 28 can be adjusted to form any number of different coating patterns on stent 10. For example, FIG. 4E illustrates layers 44 deposited in between layers 40, in bare regions 42. Again, layers 44 can be made from different polymeric materials and can optionally include the same or different therapeutic substances or combination of substances. Topcoat layer 46 can also be deposited over layers 40 and 44. FIG. 4F illustrates that layers 44 can be of any suitable length and deposited on any selected region of stent 10 by adjusting the positioning of barriers 28. As a result, customized release parameters for a variety of drugs can be achieved by producing coatings of unique layering patterns.

Representative examples of polymers that can be used to form the coating include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Representative examples of solvents can include N,N-dimethylacetamide (DMAC) having the formula $CH_3—CO—N(CH_3)_2$, N,N-dimethylformamide (DMFA) having the formula $H—CO—N(CH_3)_2$, tetrahydrofuran (THF) having the formula $C_4H_8O$, dimethylsulfoxide (DMSO) having the formula $(CH_3)_2S{=}O$, or trifluoro acetic anhydride (TFAA) having the formula $(CF_3—CO)_2O$. If multi-layered coatings are formed, the solvent of the top layer should not significantly dissolved the polymer of the underlying layer or extract the drug out from the underlying layer.

The therapeutic substance can be for inhibiting the activity of vascular smooth muscle cells. More specifically, the therapeutic substances can be aimed at inhibiting abnormal or inappropriate migration and/or proliferation of smooth muscle cells for the inhibition of restenosis. The therapeutic substances can also include any substance capable of exerting a therapeutic or prophylactic effect in the practice of the present invention. For example, the therapeutic substances can be for enhancing wound healing in a vascular site or improving the structural and elastic properties of the vascular site. Examples of therapeutic substances include antiproliferative substances such as actinomycin D, or derivatives and analogs thereof (manufactured by Sigma-Aldrich, Inc., Milwaukee, Wis.; or COSMEGEN available from Merck & Co., Inc., Whitehouse Station, N.J.). Synonyms of actinomycin D include dactinomycin, actinomycin IV, actinomycin $I_1$, actinomycin $X_1$, and actinomycin $C_1$. The active therapeutic substances can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany) methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co.). Examples of such antiplatelets, anticoagulants, antifibrins, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative therapeutic substances include angiopeptin, angiotensin converting enzyme inhibitors such as captopril (e.g., Capoten® and Capozide® from Bristol-Myers Squibb Co.), cilazapril or lisinopril (e.g., Prinivil® and Prinzide® from Merck & Co., Inc.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic therapeutic substance is permirolast potassium. Other therapeutic substances or agents which may be appropriate include alpha-interferon, genetically engineered epithelial cells, dexamethasone and rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for coating a stent, comprising:

applying a first composition to a first segment of a stent with a first nozzle assembly; and simultaneously with the application of the first composition, applying a second composition to a second segment of the stent with a second nozzle assembly, wherein the first nozzle assembly and the second nozzle assembly are separated by a barrier, wherein the barrier includes an opening through which the stent is positioned.

2. The method of claim 1, wherein the second segment of the stent does not get exposed or significantly exposed to the first composition and wherein the first segment of the stent does not get exposed or significantly exposed to the second composition when both compositions are being applied simultaneously.

3. The method of claim 1, wherein the first composition is different from the second composition in type of polymer, type of therapeutic substance, or concentration of therapeutic substance.

4. The method of claim 1, additionally including simultaneously with the application of the first and second compositions to the stent, applying a third composition by a third nozzle assembly to a third segment of the stent.

5. A method for coating a stent, comprising:

applying a first composition to a first segment of a stent with a first nozzle assembly; and simultaneously with the application of the first composition, applying a second composition to a second segment of the stent with a second nozzle assembly, and additionally including with the application of the first and second compositions to the stent, applying a third composition by a third nozzle assembly to a third segment of the stent, wherein the first and second nozzle assemblies are separated by a first barrier and the second and third nozzle assemblies are separated by a second barrier, the second nozzle assembly being positioned between the first nozzle and the third nozzle assemblies, wherein the first and second barriers include an opening through which the stent is positioned.

6. The method of claim 5, wherein the distance between the first barrier and the second barrier is adjustable.

7. The method of claim 1, additionally comprising rotating the stent about the longitudinal axis of the stent.

8. A method of coating a stent, comprising:

positioning the stent through a through hole formed in a barrier such that a first surface of the barrier faces one end of the stent and a second surface of the barrier faces an opposing end of the stent;

positioning a nozzle relative to the barrier such that the barrier shields a first area of the stent to which a coating substance is not be applied and the barrier does not shield a second area of the stent to which the first coating substance is to be applied; and delivering the coating substance from the nozzle to the second area of the stent.

9. The method of claim 8, further comprising positioning a second nozzle relative to the barrier to allow application of a second coating substance from the second nozzle to the first area of the stent but not the second area of the stent.

10. The method of claim 9, further comprising delivering the second coating substance from the second nozzle to the first area of the stent, and preventing or significantly minimizing cross-contamination of the coating substance from the nozzle and the second coating substance from the second nozzle as the coating substances are applied to the stent.

* * * * *